United States Patent [19]
Giannavola

[11] Patent Number: 5,248,537
[45] Date of Patent: Sep. 28, 1993

[54] NON-CONTAMINATING FRAGRANCE RELEASING INSERT FOR MAGAZINES

[75] Inventor: Mark R. Giannavola, Torrington, Conn.

[73] Assignee: Danbury Printing & Litho, Inc., Danbury, Conn.

[21] Appl. No.: 918,427

[22] Filed: Jul. 22, 1992

[51] Int. Cl.⁵ .......................... B32B 7/06; B32B 7/12
[52] U.S. Cl. ...................................... 428/40; 428/43; 428/126; 428/194; 428/905; 239/34
[58] Field of Search ................... 428/40, 43, 194, 405, 428/126; 239/34

[56] References Cited

U.S. PATENT DOCUMENTS

| | | | |
|---|---|---|---|
| 4,145,001 | 3/1979 | Weyenberg et al. | 239/56 |
| 4,484,768 | 11/1984 | Norfleet | 283/1 B |
| 4,487,801 | 12/1984 | Turnbull et al. | 428/313.5 |
| 4,606,956 | 8/1986 | Charbonneau et al. | 428/40 |
| 4,720,417 | 1/1988 | Sweeny et al. | 428/201 |
| 4,752,496 | 6/1988 | Fellows et al. | 427/27 |
| 4,889,755 | 12/1989 | Charbonneau | 428/42 |
| 4,925,517 | 5/1990 | Charbonneau | 156/276 |
| 4,952,400 | 8/1990 | Tararuj et al. | 424/401 |
| 5,050,910 | 9/1991 | Schechter et al. | 283/105 |

*Primary Examiner*—Alexander S. Thomas
*Attorney, Agent, or Firm*—Ware, Fressola, Van Der Sluys & Adolphson

[57] ABSTRACT

A fragrance releasing insert for magazines provides a fragrance sample to readers. The insert of the present invention is formed from a single substrate which has a removable portion which contains the fragrance sample. The removable portion forms a diffusion resistant envelope around the fragrance sample which reduces the possibility of inadvertent contamination of the magazine by fragrance. While the removable diffusion resistant envelope is attached to the remainder of the insert in the magazine, the fragrance cannot be sampled. However, after removal of the envelope along a pair of perforations, the fragrance may be sampled by peeling open the envelope, thus causing a release of the fragrance.

9 Claims, 3 Drawing Sheets

NON-CONTAMINATING FRAGRANCE RELEASING INSERT FOR MAGAZINES

FIELD OF THE INVENTION

The present invention relates to advertising inserts for magazines and the like and the method of preparing such inserts. More particularly, the present invention relates to a non-contaminating fragrance releasing insert having a removable portion containing microencapsulated fragrances adhered therein.

BACKGROUND OF THE INVENTION

The use of fragrance releasing pull apart sheets is known as well as the use of fragrance releasing inserts in magazines for providing fragrance samples. U.S. Pat. No. 4,925,517 discloses fragrance releasing pull-apart sheets coated with a binder on opposing surfaces where fragrance containing microcapsules are placed, and where the opposing surfaces are bound by the binder and/or additional adhesive applied with the microcapsules. U.S. Pat. No. 4,889,755 discloses a fragrance releasing pull-out sampler wherein encapsulated fragrances are provided as samples by binding a removable strip between two cover sheets. The strip is adhesively secured on at least one face to the inside of the cover sheets by an adhesive bearing microencapsulated liquid. The sampler disclosed therein is typically attached into a magazine by well known binding methods. The reader of a magazine interested in sampling the fragrance pulls the strip from the cover sheets. The separation of the microcapsule containing adhesive causes the microcapsules to break and release fragrance. Because the adhesive is used to bind the sampling strip to the cover sheet, some of the microcapsules remain with the cover sheet inside the magazine and, thus, contaminate the magazine with fragrance from the ruptured microcapsules. If many of these samplers are included in a magazine, the entire magazine tends to have a strong composite odor of many scents rather than having the ability to provide the reader with many distinct samples of individual scents. Furthermore, some readers are allergenically sensitive to such scents and have allergic reactions to such fragrances when exposed to the remaining insert coversheets of a magazine wherein the fragrance sampler inserts have been sampled. The Postal Service requires that the distribution of fragrance samplers be in enclosures which are sufficiently sealed so as to protect consumers from inadvertent inhalation. See Federal Register Vol. 56 No. 89 §§ 124.395 and 124.396. In response, distributors have enclosed such samplers in a cellophane envelope to avoid liability for inadvertent inhalation. However, such envelopes add expense to the distribution process for fragrance samples. The present invention provides a fragrance releasing insert for sampling fragrances which prevents the inadvertent inhalation of fragrance residue left on a sampled insert without the use of cellophane envelopes.

SUMMARY OF THE INVENTION

The present invention relates to a fragrance releasing insert for magazines which provides a fragrance sample to readers. The insert of the present invention is formed from a single substrate which has a removable portion which contains the fragrance sample. The removable portion forms a diffusion resistant envelope around the fragrance sample which reduces the possibility of inadvertent contamination of the magazine by fragrance. While the removable diffusion resistant envelope is attached to the remainder of the insert in the magazine, the fragrance cannot be sampled. However, after removal of the envelope along a pair of perforations, the fragrance may be sampled by peeling open the envelope, thus causing a release of the fragrance.

The non-contaminating fragrance releasing insert for magazines is manufactured from a single substrate having four edges and two surfaces to which a barrier coating is applied to a portion of a first surface of the substrate. A slurry of adhesive containing microencapsulated fragrance is applied to a portion of the barrier coating adjacent to a first end of the barrier coating. A breakaway adhesive is applied to a portion of the barrier coating adjacent to a second end. A first adhesive is applied to a portion of the first side of the substrate at a second end. A first fold is made to the substrate at a point on the barrier coating, wherein after folding said substrate about said first fold, said first surface, said first fold and said breakaway adhesive form an envelope surrounding the microencapsulated fragrance adhesive slurry, wherein said first adhesive at said second end binds to a portion of said first surface of said substrate, and wherein a portion of a second surface, opposite to said first side of said substrate overlaps a portion of said first surface. A second wet stream glue is applied to a portion of a forth edge of said substrate on the second surface. A perforation is made along a portion of the substrate proximal to said second wet stream glue. A plurality of adhesive breakaway tabs are applied to the second surface of said substrate proximal to said first fold. A second fold is made to said substrate at a point between said perforation and said second adhesive wherein said second adhesive binds the second side of said substrate, and wherein the plurality of adhesive tabs adhere said second surface of the substrate to said first surface of said substrate.

One objective of the present invention is to provide a fragrance releasing insert for a magazine.

Another objective of the present invention is to provide a non-contaminating fragrance releasing insert for a magazine.

Still yet another objective of the present invention is to provide a non-contaminating fragrance releasing insert for a magazine wherein the fragrance cannot be sampled while the fragrance remains attached to the magazine.

Other objects and advantages of the present invention will become apparent to those skilled in the art from the following detailed description read in conjunction with the attached drawings and claims appended hereto.

DETAILED DESCRIPTION OF THE INVENTION

Figure 1:
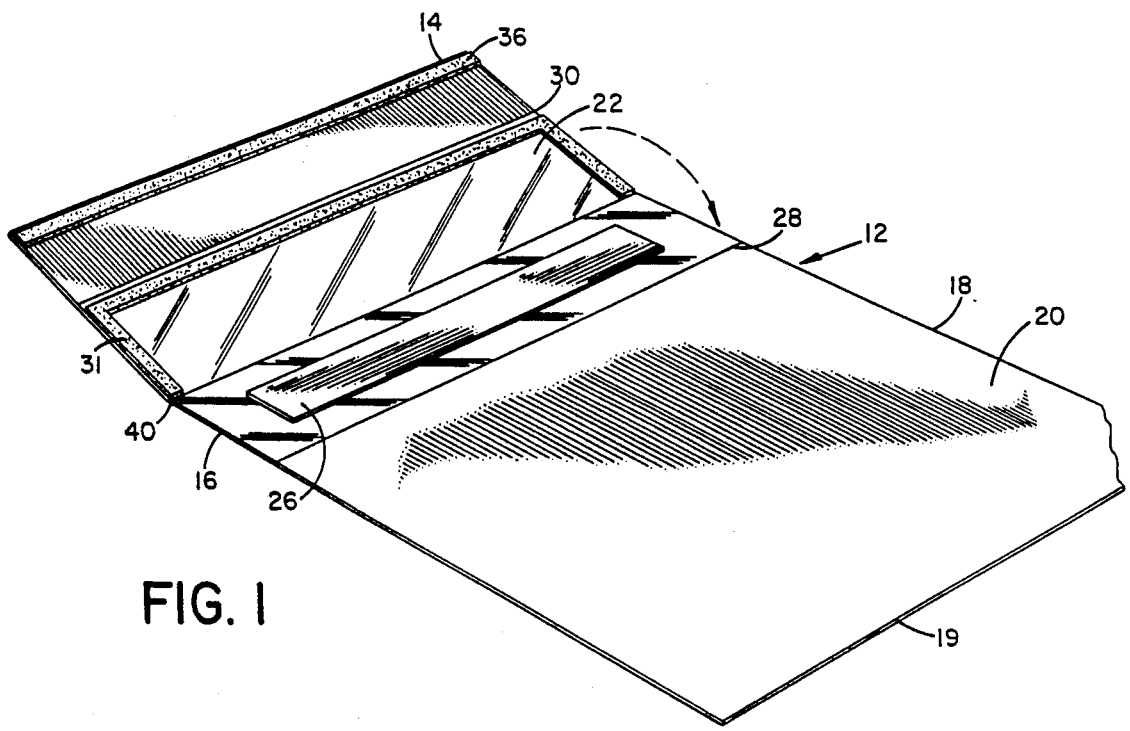
FIG. 1 is an isometric view of a partially folded substrate about a first fold showing the substrate having a barrier coating, a fragrance adhesive strip, a barrier glue strip and a first wet glue strip applied thereon.
Figure 2:
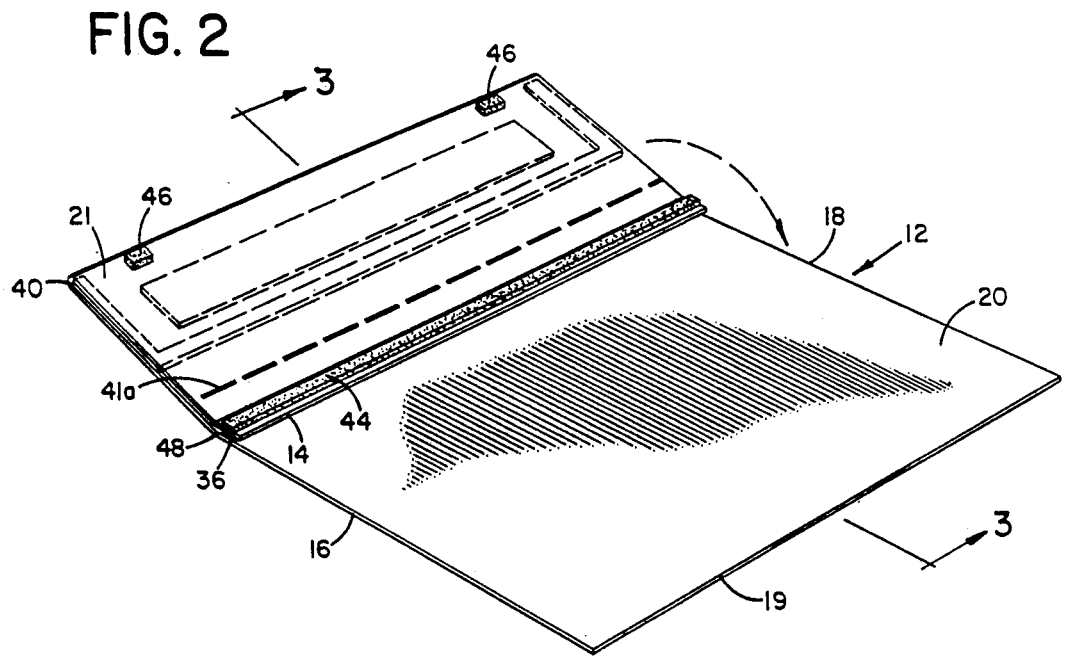
FIG. 2 is an isometric view of the substrate partially folded about a second fold of the present invention showing a second wet stream glue and a plurality of adhesive tabs, and showing a perforation proximal to the second fold.
Figure 3:
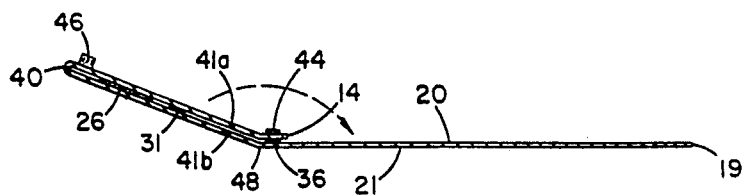
FIG. 3 is a view taken along the line 3—3 of FIG. 2 and illustrates the relative positioning of the folds.
Figure 4:
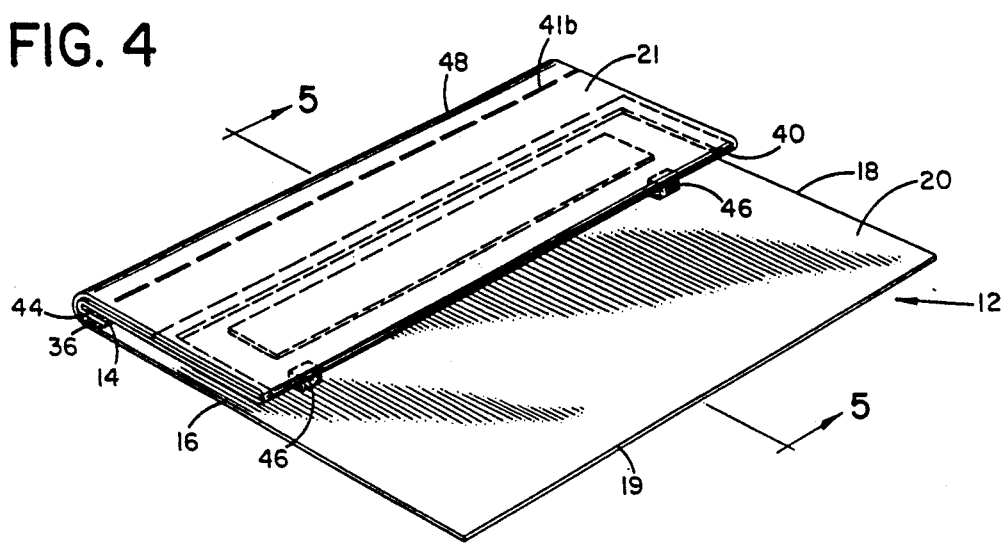
FIG. 4 is an isometric view of the substrate fully folded about the second fold and shows the perforation proximal to the second fold.
Figure 5:
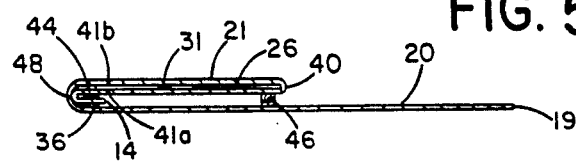
FIG. 5 is a view taken along the line 5—5 of FIG. 4 and illustrates the relative positioning of the folds.

Now referring to FIGS. 1, 2, 3, 4 and 5, the non-contaminating fragrance releasing insert 10 of the present invention may be constructed from a single paper substrate 12 having a first edge 14, a second edge 16, a third edge 18, a forth edge 19, a first surface 20 and a second surface 21. The insert is fabricated by first applying an aqueous styrene-acrylic emulsion polymer dispersion strip 22, such as Cork Coat TM CK-2507, to a portion of the first surface 20 of the substrate from the second edge 16 to the third edge 18. The barrier coating strip 22 is applied in an amount so as to have a 1 millimeter thickness on the first surface 20 of the substrate. The barrier coating is then heated for a period of time to a temperature in the range of 250° to 350° so as to cure the aqueous polymer dispersion on the first surface 20. The barrier coating provides a diffusion proof seal on the first surface of the substrate so as to prevent diffusion of a later applied fragance adhesive described more fully below.

After the barrier coating is applied, a microencapsulated fragrance adhesive slurry is applied as a strip 26 approximately 1 millimeter thick over a portion of the barrier coating and proximal to a first end 28 of the barrier coating. Preferably, the center of the fragrance strip 26 is positioned at a point on the barrier coating which is one-quarter of the distance from the first end 28 to a second end 30 and, although not necessary to practice the invention, the width of the strip is less than one half of the width of the barrier coating. Also, the length of the fragrance strip 26 is shorter than the distance from the second edge 16 to the third edge 18 so as to leave a small margin between each edge and the slurry strip 26. It can be appreciated by those skilled in the art that the application of the fragrance strip 26 proximal to the second end 30 of the barrier coating strip 22 rather than proximal to the first end 28 will not deviate from the spirit of the present invention.

Next, a breakaway glue strip 31 comprising a formulated ethylenevinyl acetate adhesive, such as National Adhesives' NAtional TM 33-9080 or a formulated polyvinyl acetate adhesive such as National TM 32-1709, is applied proximal and approximately parallel to the second end 30 of the barrier coating strip, and proximal and approximately parallel to the second edge 16 and third edge 18 of the substrate up to approximately the midpoint between the first end 28 and the second end 30 of the barrier coating strip 22. Of course, the breakaway glue strip 31 may be applied proximal to the first end of the barrier coating strip 22 in the same manner described above without deviating from the spirit of the present invention.

Following the application of the breakaway gluestrip, a wet stream glue strip 36 comprising a formulated polyvinyl acetate adhesive, such as National Adhesives' Royaldex TM 32-3419, is applied to a portion of the first surface 20 of the substrate at the first edge 14. After the wet stream glue strip 36 is applied, the substrate is folded about a first fold 40 which is approximately at the midpoint between the first end 28 and the second end 30 of the barrier coating strip 22. After folding about the first fold 40, the first surface 20, the first fold 40 and the breakaway glue strip 31 form an envelope around the fragrance slurry 26. Also, after the first fold, the wet glue stream 36 binds the first surface proximal to the first edge 14 to another portion of the first surface of the substrate so as to allow a portion of the second surface 21 of the substrate to be coplanar with the first surface.

Next, two perforations 41a, 41b which extend from the second edge 16 to the third edge 18 are together made on a portion of the substrate 12 where the second surface 21 overlaps the first surface 20. The perforations 41a, 41b are made singly after the first fold so as to have two aligned perforations running through the overlapping portion of the substrate. The perforation allow a portion of the substrate containing the fragrance slurry strip to be easily removed from the remaining portion of the substrate. After perforating the substrate, a second wet stream glue strip 44 is applied proximal to the first edge 14 of the substrate on the second surface 21. A plurality of breakaway glue tabs 46 are applied on the second surface of the substrate proximal to the first fold 40. The substrate is then folded about a second fold 48. The second fold 48 is positioned between the perforations 41a and 41b and the second wet stream glue 44. After the substrate is folded about the second fold 48, the second wet stream glue strip 44 binds two portions of the second surface of the substrate and the plurality of glue tabs 46 bind a portion of the second surface 21 proximal to the first fold 40 to a portion of the first surface 20 of the substrate.

Figure 6:
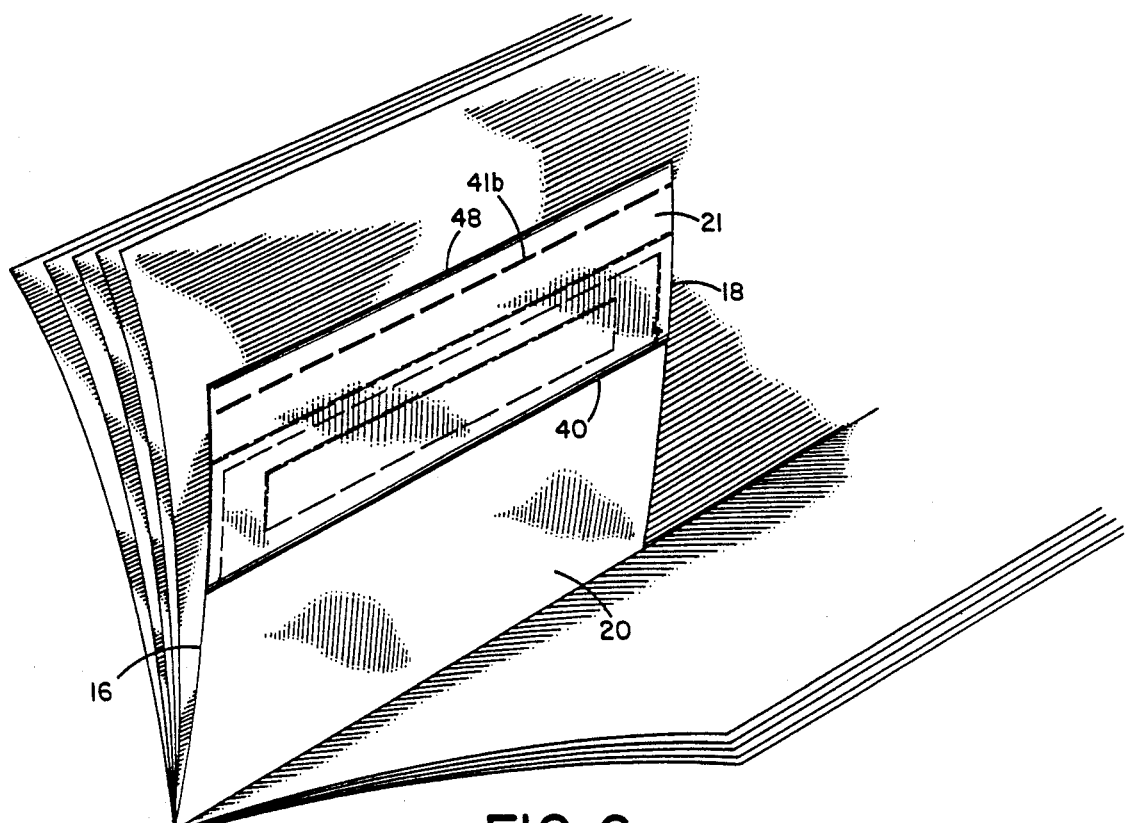
FIG. 6 is an illustration of the fragrance releasing insert of the present invention inserted into a magazine.
Figure 7:
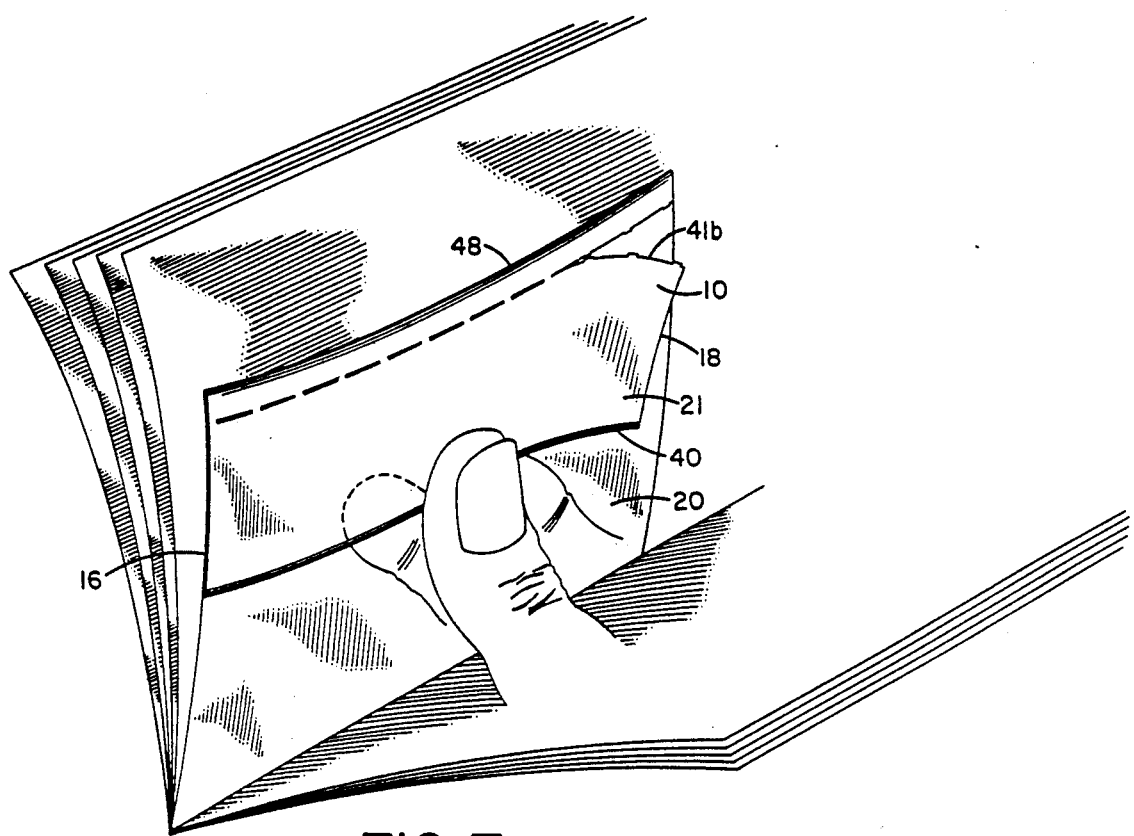
FIG. 7 is an illustration of the fragrance releasing insert of the present invention wherein the fragrance containing portion of the insert has been separated along the perforations and removed.
Figure 8:
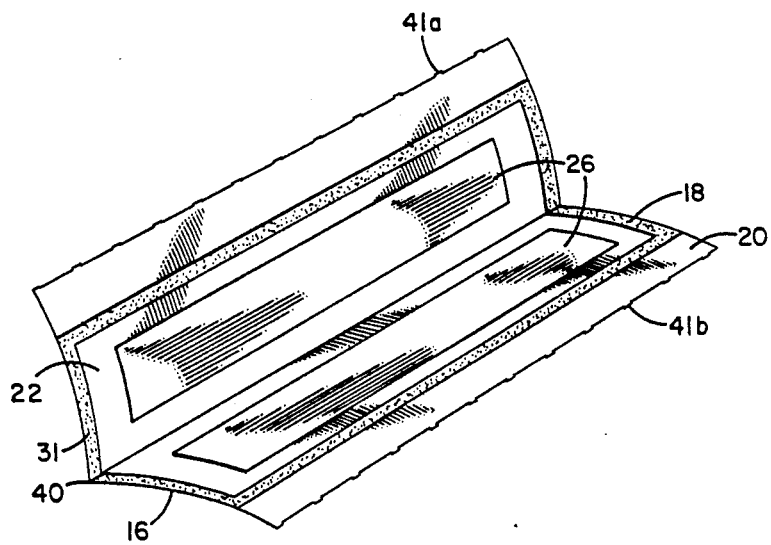
FIG. 8 is an illustration of the fragrance containing portion of the insert of the present invention, wherein the fragrance containing portion has been separated from the magazine and has been opened to expose the fragrance releasing strip.

After the second fold is made and the adhesives have cured, the fragrance releasing insert 10 is ready for binding into a magazine or other like publication. The forth edge 19 of the insert is bound to the magazine by well known binding methods including perfect binding or saddle switching. FIGS. 6, 7 and 8 show a magazine with the entire insert attached thereto, the same magazine with the fragrance slurry containing portion removed along the perforations 41a and 41b and the fragrance containing portion opened to permit sampling of the fragrance. Referring to FIGS. 1, 6, 7 and 8, because the fragrance strip is surrounded on three sides by the breakaway glue 31 and the first fold 40 on the forth and remaining side, the fragrance of the insert may only be sampled by separating, at the perforations 41a and 41b, the portion of the insert containing the fragrance strip 26 from the remaining portion of the insert. Once the portion of insert containing the fragrance strip is removed, it may be sampled by simply peeling apart the substrate bound by the breakaway glue strip 31 and the fragrance strip 26. Thus, the fragrance releasing insert of the present invention prevents contamination of the magazine because once the fragrance strip containing portion is removed from the remainder of the insert, it cannot be simply reattached.

Thus, what has been described is a non-contaminating fragrance releasing insert for magazines having a removable portion for sampling fragrances. While the preferred embodiment of the present invention has been described and illustrated, it is understood by someone skilled in the art that the preferred embodiment is capable of variation, addition, omission, and modification without departing from the spirit and scope of the invention.

What is claimed is:

1. A fragrance releasing insert for magazines, comprising:

a substrate having a first edge, a second edge, a third edge, a forth edge, a first surface and a second surface, wherein said first edge is opposite of said forth edge and said second edge is opposite of said third edge;

a barrier coating, wherein said barrier coating is applied to a portion of said first surface of said substrate, wherein said barrier coating has a first end proximal to said first edge of said substrate and has a second end proximal to said forth edge of said substrate;

a fragrance containing adhesive, wherein said fragrance containing adhesive is applied to a portion of said barrier coating;

a pattern breakaway adhesive, wherein said pattern breakaway adhesive is applied to a portion of said barrier coating strip, wherein said pattern breakaway adhesive substantially surrounds said fragrance containing adhesive strip;

a first adhesive, wherein said first adhesive is applied to a portion of said first surface of said substrate proximal to said first edge;

a first fold, wherein said first fold is positioned on said barrier coating and extends from said second edge to said third edge of said substrate, wherein a portion of said first surface proximal to said first edge faces and is adhered to a portion of said first surface, wherein a portion of said second surface proximal to said first edge overlaps a portion of said first surface, and wherein said first surface, said pattern breakaway adhesive and said first fold completely surround said fragrance containing adhesive;

a second adhesive, wherein said second adhesive is applied to a portion of said second surface of said substrate proximal to said first edge;

a third adhesive, wherein said third adhesive is applied to a portion of said second surface of said substrate proximal to said first fold;

a perforation, wherein said perforation is positioned on a portion of said substrate where said second surface overlaps said first surface, wherein said perforation extends from said second edge to said third edge and wherein said perforation extends entirely through said overlapping portions of said substrate;

a second fold, wherein said second fold is positioned between said second adhesive and said perforation, wherein said second fold extends from said second edge to said third edge of said substrate, wherein said third adhesive is adhered to a portion of said first surface of said substrate, and wherein said second adhesive is adhered to a portion of said second surface.

2. The fragrance releasing insert of claim 1, wherein said barrier coating is a styreneacrylic polymer.

3. The fragrance releasing insert of claim 2, wherein said polymer is Cork Coat CK-2507.

4. The fragrance releasing insert of claim 1, wherein said first adhesive is a continuous strip extending from said second edge to said third edge of said substrate.

5. The fragrance releasing insert of claim 1, wherein said second adhesive is a continuous strip extending from said second edge to said third edge of said substrate.

6. The fragrance insert of claim 1, wherein said third adhesive is a plurality of adhesive tabs extending from said second edge to said third edge of said substrate.

7. The fragrance releasing insert of claim 1, wherein said third adhesive is a continuous strip extending from said second edge to said third edge of said substrate.

8. The fragrance releasing insert of claim 1, wherein said fragrance containing adhesive is a continuous strip, wherein said strip is centered approximately at a point on the barrier coating which is three-quarters of the distance between said first end and said second end of said barrier coating, wherein said strip has a length shorter than the distance from said second edge to said third edge so as to provide a margin between said second edge and said strip and a margin between said third edge and said strip, and wherein said strip has a width which is less than one half the distance between said first end and said second end of said barrier coating.

9. The fragrance releasing insert of claim 1, wherein the fragrance of said fragrance containing adhesive is contained in rupturable microcapsules dispersed in said adhesive.

* * * * *

UNITED STATES PATENT AND TRADEMARK OFFICE
CERTIFICATE OF CORRECTION

PATENT NO. : 5,248,537
DATED : September 28, 1993
INVENTOR(S) : Mark R. Giannavola It is certified that error appears in the above-identified patent and that said Letters Patent is hereby corrected as shown below:

At column 4, line 46, please change "switching" to --stitching--

At column 6, line 27, after "fragrance", please insert --releasing--

Signed and Sealed this

Fifteenth Day of March, 1994

Attest:

BRUCE LEHMAN

Attesting Officer   Commissioner of Patents and Trademarks